(12) United States Patent
Platzek et al.

(10) Patent No.: US 6,677,483 B2
(45) Date of Patent: Jan. 13, 2004

(54) PROCESS FOR THE PRODUCTION OF MONOAMIDES OF DTPA

(75) Inventors: Johannes Platzek, Berlin (DE); Ulrich Niedballa, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/056,044

(22) Filed: Jan. 28, 2002

(65) Prior Publication Data
US 2002/0155065 A1 Oct. 24, 2002

Related U.S. Application Data
(60) Provisional application No. 60/268,059, filed on Feb. 13, 2001.

(30) Foreign Application Priority Data

Jan. 26, 2001 (DE) .......................................... 101 05 014

(51) Int. Cl.[7] ...................... C07C 229/00; C07D 413/00
(52) U.S. Cl. ...................... 562/565; 544/111; 544/147
(58) Field of Search .......................... 562/565; 564/144, 564/152, 155, 193, 194; 544/111, 147

(56) References Cited

U.S. PATENT DOCUMENTS

| | | | |
|---|---|---|---|
| H1312 H | | 5/1994 | Coughlin et al. |
| 5,453,264 A | * | 9/1995 | Mori et al. ............... 424/9.364 |
| 5,571,498 A | | 11/1996 | Cacheris et al. |
| 5,679,810 A | * | 10/1997 | Love et al. .................. 560/171 |
| 5,843,399 A | * | 12/1998 | Gries et al. .............. 424/9.364 |
| 6,045,776 A | | 4/2000 | Platzek et al. |

FOREIGN PATENT DOCUMENTS

WO   WO87/02708 A1   7/1987

\* cited by examiner

*Primary Examiner*—Mukund J. Shah
*Assistant Examiner*—Zachary C. Tucker
(74) *Attorney, Agent, or Firm*—Millen, White, Zelano & Branigan

(57) ABSTRACT

A new process for the preparation of diethylenetriaminepentaacetic-monoamides in which amines can be reacted with sensitive groups, a higher mono/diamide selectivity is achieved, a higher yield of monoamide is achieved and has a simple reaction scheme and working-up.

20 Claims, No Drawings

PROCESS FOR THE PRODUCTION OF MONOAMIDES OF DTPA

This application claims the benefit of the filing date of U.S. Provisional Application Serial No. 60/268,059 filed Feb. 13, 2001.

This invention describes a new process for the preparation of diethylenetriaminepentaacetic acid-monoamides (DTPA-monoamides) Monoamides of DTPA are described extensively in the literature. They are used as complexing agents for metal complexes, which have come to be used in imaging diagnosis. Thus, for example, the compound 3,6-bis(carboxymethyl)-9-(10-carboxydecylcarbamoyl-methyl)-3,6,9-triazaundecanoic acid"mono-puchel" is described in EP 450 742 as a potential liver contrast medium. Other monoamides of DTPA for visualizing organs are found in WO 95/27705, EP 529 175, WO 95/33494. Aromatic amides for liver diagnosis (MRI) were described by the Green Cross Company in EP 603 403, U.S. Pat. Nos. 5,453,264 and 5,575 986. In addition, other compound classes, such as, e.g., blood pool contrast media, were described (polylysine-DTPA, EP 331 616, dendrimers EP 430 863), which contain monoamides of DTPA.

In the above-mentioned bibliographic references as well as in special process patents, different methods for the production of: monoamides (starting from DTPA) were described, as in U.S. Pat. No. 5,021,571 or in EP 263 059, formula diagram 1:

Formula Diagram 1

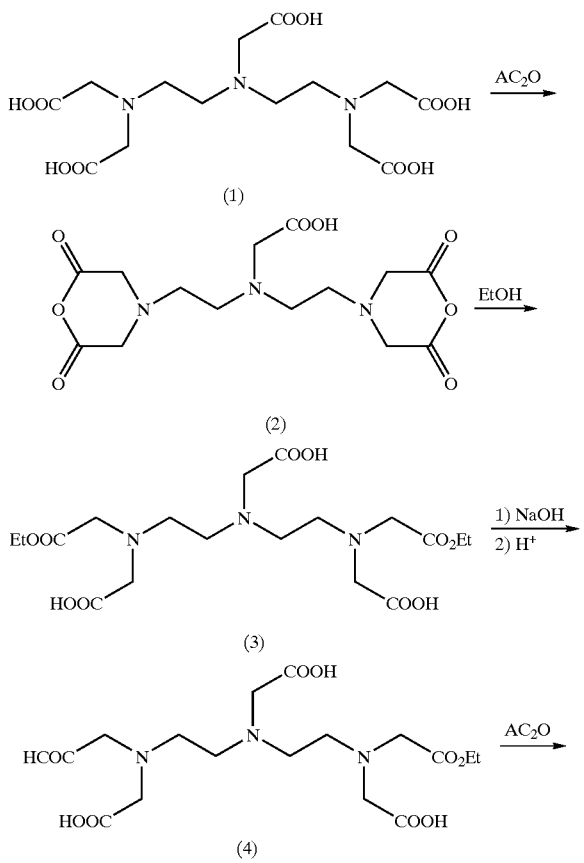

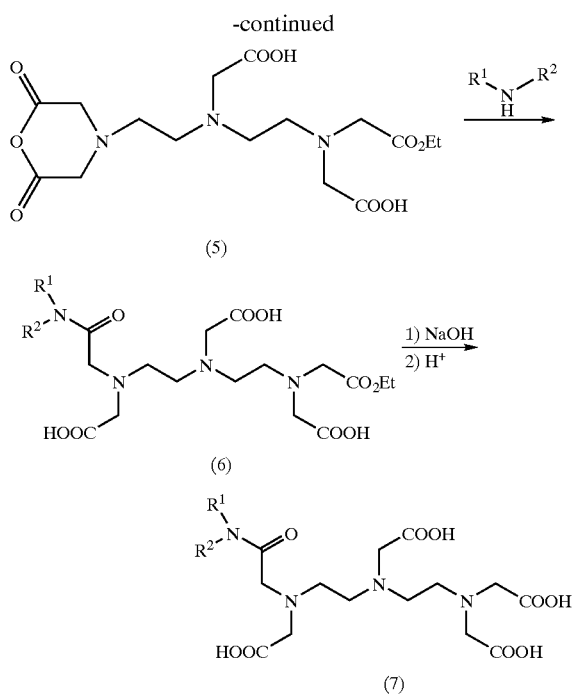

The thus obtained monoamides are obtained in a total of six stages. The total yield is relatively low, since the yield of intermediate product (4) is greatly reduced by the partial saponification of the ester groups and the subsequent chromatography.

Other authors describe the production of DTPA tetraesters (U.S. Pat. No. 5,412,148, WO 94/03593, DE 19508058, DE 19507819, U.S. Pat. No. 6080785), in which compounds of general formula (8)

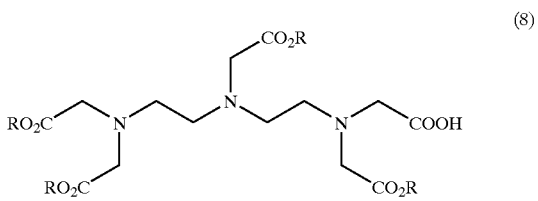

have to be produced by longer synthesis sequences (in some cases more than five stages). The compounds of general formula (8) are converted into the corresponding active esters of acid and then reacted with an amine HN $R^1R^2$ to form the protected monoamides of formula (9)

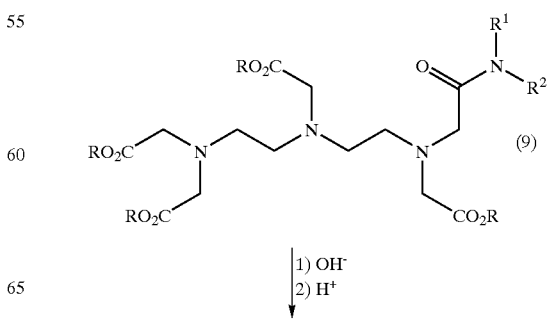

-continued

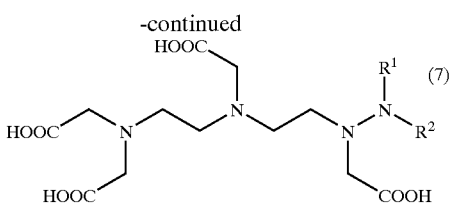

(7)

The subsequent ester saponification and acidic working-up yield the desired monoamides with free carboxylic acids. A disadvantage to both above-described processes is the fact that ester groups that can be contained in the amine of general formula $R^1R^2$ are also saponified by the downstream saponification step. The use of t-butyl esters or benzyl esters is also problematical in nature, since in the case of acidic or reductive cleavage, radicals $R^1$ and $R^2$ are attacked.

Krejcarek follows another method. Krejcarek starts from the DTPA, produces a pentaamonium salt and reacts the latter with one equivalent of chloroformic acid ester to form the mono-mixed anhydride of DTPA and then with one amine [Krejcarek and Tucker, Biochem. Biophys. Res. Commun. 77, 581 (1977), WO 91/05762]. It is disadvantageous in this process that it cannot be determined whether the amide formation takes place on one of the terminal acetic acids or on the central acetic acid. In addition, the high accumulation of by-products is disadvantageous in this process. Five equivalents of amine salt must be removed, four of which were not involved in the activation of that of the carbonyl group.

Processes that start from bisanhydride of DTPA (2) are also known from the patent literature:

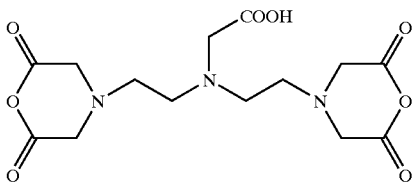

(2)

The selective conversion of the bisanhydride of DTPA (2) to form monoamides by adding one equivalent of water, which presumably converts monoanhydride (10), was described in the Patents (U.S. Pat. Nos. 5,559,214, 5,871,710, 5,593,658, EP 451 824).

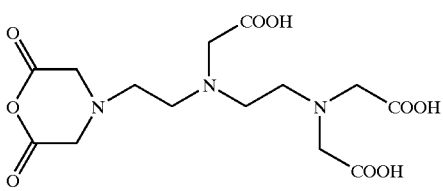

(10)

Hnatowich has already described the immediate reaction of bisanhydride (2) with amines in aqueous buffer (U.S. Pat. No. 4,479,930).

It is disadvantageous that large excesses of bisanhydride are necessary to produce a selective reaction, and the saponification in water is also a problem. Reactions of bisanhydride (2) in DMF with the addition of pyridine or another base were also described (U.S. Pat. No. 5,571,498, WO 95/33494, WO 96/16679). It is problematical in such reactions that they are performed at an elevated temperature (50–100° C.), which is disadvantageous for sensitive amines, and that they show very low selectivities relative to the formation of the monoanhydride. Even if excess (2–5 equivalents) bisanhydride (2) relative to HN $R^1R^2$ is used, the main product in all cases is the bisamide (11)

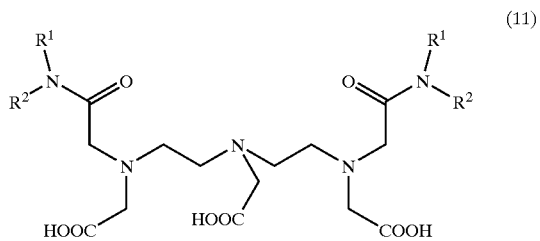

(11)

The monoamide that is formed in the first step obviously has a higher solubility and is therefore more reactive than the bisanhydride that is present in excess and is preferably reacted off. The latter is observed in solvents such as DMF, DMSO, formamide. In the case of reactions of <50° C., e.g., room temperature, the formation of (11) is observed almost exclusively.

Based on the above-described drawbacks, a need for a new process for the production of monoamides existed, in which 1) Amines can be reacted with sensitive groups (esters, easily saponifying, reducing, temperature-sensitive groups)

2) A higher mono/diamide selectivity is achieved

3) A higher yield of mono-amide is achieved

4) A simple reaction scheme and working-up is achieved.

These requirements are met by this process.

The invention relates to a process for the production of monoamides of DTPA of general formula (I)

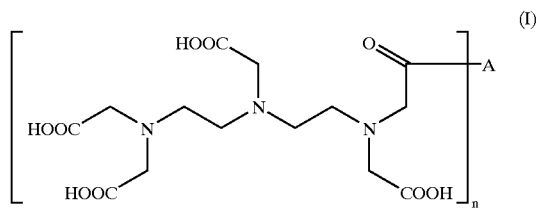

(I)

in which n stands for numbers 1 or 2,

A stands for, when n=1, a primary, secondary, aliphatic, aromatic or araliphatic monoamine that is reduced by a hydrogen atom on a nitrogen atom, or for, when n=2, a primary, secondary, mixed primary/secondary, aliphatic, aromatic, araliphatic or mixed aliphatic/aromatic/araliphatic diamine that is reduced in each case by a hydrogen atom on the two nitrogen atoms, comprising the DTPA-bisanhydride of formula (2)

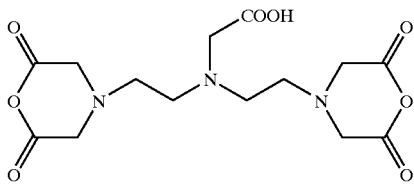
(2)

is dissolved in dimethyl sulfoxide (DMSO) or dimethylformamide (DMF) or mixtures thereof with the addition of an inorganic or organic solubilizer in homogeneous solution, with the addition of an auxiliary base with a monoamine (n=1) or diamine (n=2) of general formula II $$A(H)_n \qquad (II)$$

in which n and A have the above-mentioned meaning, and is reacted at temperatures of 10–70° C. for a reaction time of 1–24 hours.

The solubilizer is used in amounts of 1–10, preferably 2–5 equivalents, relative to the DTPA-bisanhydride (2). The homogeneous solution that comprises the DTPA-bisanhydride (2) and the solubilizer in DMSO, DMF or mixtures thereof that is obtained by heating (up to 150° C.) is allowed to cool to the desired reaction temperature and then mixed with amine II, and is optionally dissolved in a solvent, such as, e.g., DMSO, DMF, pyridine, dioxane, tetrahydrofuran or mixtures thereof. A reaction temperature of 15–50° C. and a reaction time of 3–8 hours are preferred.

In addition to ammonia (in most cases dissolved in a solvent), amines of natural or synthetic origin are used as amines: primary, secondary, aliphatic, aromatic, araliphatic monoamines and diamines, whereby in the case of diamines, mixed primary/secondary or mixed aliphatic/aromatic/araliphatic diamines can occur. Amines of natural origin occur, i.a., from the classes of steroids, alkaloids, peptides, amino acids, nucleotides, nucleosides, porphyrins and carbohydrates.

| Amines of Type A(H) | |
|---|---|
| Aniline | 4-Bromoaniline |
| 4-Methylaniline | 3-Trifluoromethylaniline |
| 2-Ethoxycarbonylaniline | 4-Cyclohexylaniline |
| 4-Decylaniline | 4-Methoxyaniline |
| 4-Nitroaniline | 4-Phenylaniline |
| 3,5-Bistrifluoromethylaniline | $CH_3\text{—}(CH_2)_{n=0-9}\text{—}NH_2$ |
| 5-Aminoisophthalic acid diethyl ester | $NH_2CH_2\text{—}CHOH\text{—}CHOH\text{—}CH_2OH$ |
| Ammonia | Morpholine |
| 4-N-(Methylamino-methyl-2,2-dimethyl-1,3-dioxolane | |
| N-(2-Aminoethyl)-morpholine | 4-(4-Fluoro)-phenyl-piperazine |
| Piperidine | 2-Piperidinocarboxylic acid benzyl ester |
| 4-Ethoxycarbonylpiperidine | 2-Ethoxyethylamine |
| 11-Aminoundecanoic acid ethyl ester | 2-Amino-1,3-propanediol |
| 4-Phenylpiperidine | Indoline |
| Tetrahydroquinoline | 2-Deoxy-2-aminoglucose |
| Alanine benzyl ester | Dibutylamine |
| Glycine-t-butylester | 4-Aminopyridine |
| Benzylamine | 2-Aminopropionic acid ethyl ester |
| Cytidine | Adenosine |
| 2-Phenylethylamine | 9-Aminoacridine |

| Amines of Type A(H) | |
|---|---|
| 9-Aminoanthracene | Iminostilbene |
| Carbazole | 1-Aminoadamantane |
| 3-Aminomethyl-2,2,5,5-tetramethylpyrrolidine-1-yloxy | |

| Amines of Type $A(H)_2$ | |
|---|---|
| Hydrazine | $H_2N\text{—}(CH_2)_{n=2-10}\text{—}NH_2$ |
| 1,4-Bisaminomethylbenzene | Homopiperazine |
| 3,6-Diaminoacridine | 4,4'-aminomethylbenzidine |
| 2,5-Diazabicyclo[2.2.1]-heptane | 1,4-diaminocyclohexane |
| Mesoporphyrin IX-13,17-dihydrazide | Cu-Mesoporphyrin IX-13,17-dihydrazide |

Especially preferred are 4-Decylaniline, 11-Aminoundecanoic acid ethyl ester, Mesoporphyrin IX-13,17-dihydrazide and Cu-Mesoporphyrin IX-13,17-dihydrazide The auxiliary base can either be introduced or added together with the amine $A(H)_n$. It is also possible to use the amines in the form of their salts. In this case, however, excess auxiliary base is necessary. In cases where DMSO is used as a solvent, the following solubilizers are used:

| | |
|---|---|
| Inorganic: | Lithium chloride, lithium bromide, lithium iodide, lithium mesylate, lithium tosylate |
| Organic: | Phase transfer salts: $NR^{4+}Hal^-$ with R = $C_1$–$C_6$ alkyl |
| | Hal = chlorine, iodine, bromine |
| | Imidazole, phenylimidazole, N-methyl-imidazole, 4-nitrophenol, pentafluorophenol, N-hydroxysuccinimide, N-hydroxy-phenyl-triazole |

In cases where DMF is used as a solvent, imidazole is used as a solubilizer. As an auxiliary base, organic bases such as pyridine, triethylamine, N-ethyl-morpholine and imidazole are preferably used. DTPA-bisanhydride can be reacted at concentrations of up to 30%. It has also proven advantageous to increase the amount of solubilizer at concentrations of between 20–30%. For working-up, some water is added (1 equivalent and more), either concentrated by evaporation in a vacuum or else precipitated with a solvent such as diethyl ether, acetone, methyl-t-butyl ether (MTB), diisopropyl ether, tetrahydrofuran (THF) or mixtures of the latter, and the precipitate is filtered off. Then, after dissolution and adjustment of the pH, the desired product can be purified chromatographically by crystallization, by ion-exchange chromatography, by chromatography on silica gel or RP-material.

In some cases, it has proven advantageous to dry the above-obtained precipitate, to make a determination of HPLC purity and to go into the next stage with the crude product (e.g., when complexing with metals).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1

3,6,9-Tris(carboxymethyl)-3,6,9-triazaundecanedioic acid-1-carboxy-11-N-(phenyl)-amide 35.7 g (100 mmol) of DTPA-bisanhydride is dissolved in 350 ml of dimethyl sulfoxide while 12.72 g (300 mmol) of lithium chloride is added (while heated slightly). It is allowed to cool to 20° C., and a mixture that consists of 9.31 g (100 mmol) of aniline and 23.7 g (300 mmol) of pyridine is added in drops within 30 minutes. It is stirred for 4 hours at 20° C. 1.8 g (100 mmol) of water is added, and it is stirred for 10 minutes. A mixture that consists of 300 ml of acetone/2000 ml of methyl-tert-butyl ether (MTB) is added in drops to this solution and stirred for one hour at room temperature. The deposited precipitate is filtered off, washed twice with a little acetone and dried (in a vacuum/50° C.). For purification, it is chromatographed on silica gel (mobile solvent: methanol/chloroform/formic acid=20:10:1). It is absorptively precipitated with isopropanol/formic acid (20:1), the precipitate is suctioned off and dried in a vacuum/60° C.

The HPLC of the crude product yielded a monoamide:diamide ratio of 70:30.
Yield: 24.0 g (51% of theory) of a colorless solid
Water content: 0.5%
HPLC purity:>97%
Elementary analysis (relative to anhydrous substance):
Cld: C 51.28 H 6.02 N 11.96
Fnd: C 51.45 H 6.18 N 11.81

EXAMPLE 2

3,6,9-Tris(carboxymethyl)-3,6,9-triazaundecanedioic acid-1-carboxy-11-N-(morpholine)-amide 35.7 g (100 mmol) of DTPA-bisanhydride is dissolved in 350 ml of dimethyl sulfoxide while 12.72 g (300 mmol) of lithium bromide is added (while heated slightly). It is allowed to cool to 40° C., and a mixture that consists of 8.71 g (100 mmol) of morpholine and 20.24 g (200 mmol) of triethylamine is added in drops within 30 minutes. It is stirred for 6 hours at 40° C. It is cooled to room temperature, 1.8 g (100 mmol) of water is added, and it is stirred for 10 minutes. A mixture that consists of 200 ml of acetone/1800 ml of methyl-tert-butyl ether (MTB) is added in drops to this solution, and it is stirred for one hour at room temperature. The deposited precipitate is filtered off, washed twice with a little acetone and dried (in a vacuum/50° C.). For purification, it is chromatographed on silica gel (mobile solvent: methanol/chloroform/formic acid=20:10:1). It is stirred with isopropanol/formic acid (20:1), the precipitate is suctioned off and dried in a vacuum/60° C.

The HPLC of the crude product yielded a monoamide:diamide ratio of 71:29.
Yield: 24.2 g (52% of theory) of a colorless solid
Water content: 0.8% of theory
HPLC purity:>97%
Elementary analysis (relative to anhydrous substance):
Cld: C 46.75 H 6.54 N 12.12
Fnd: C 46.58 H 6.73 N 12.01

EXAMPLE 3

3,6,9-Tris(carboxymethyl)-3,6,9-triazaundecanedioic acid-1-carboxy-11-N-[(4-decyl)-phenyl]-amide 35.7 g (100 mmol) of DTPA-bisanhydride is dissolved in 350 ml of dimethyl sulfoxide while 12.72 g (300 mmol) of lithium chloride is added (while heated slightly). It is allowed to cool to 35° C., and a mixture that consists of 23.3 g (100 mmol) of 4-decyl-aniline and 23.7 g (300 mmol) of pyridine (dissolved in 25 ml of dimethyl sulfoxide) is added in drops within 30 minutes. It is stirred for 5 hours at 35° C. It is cooled to room temperature, 1.8 g (100 mmol) of water is added, and it is stirred for 10 minutes. A mixture that consists of 200 ml of acetone/2000 ml of methyl-tert-butyl ether (MTB) is added in drops to this solution, and it is stirred for one hour at room temperature. The deposited precipitate is filtered off, washed twice with a little acetone and dried (in a vacuum/50° C.). For purification, it is chromatographed on silica gel (mobile solvent: methanol/chloroform/formic acid=20:20:2). It is absorptively precipitated with acetone/formic acid (20:1), the precipitate is suctioned off and dried in a vacuum/60° C.

The HPLC of the crude product yielded a monoamide:diamide ratio of 70:30.
Yield: 30.7 g (50% of theory) of a colorless solid
Water content: 0.9%
HPLC purity:>98%
Elementary analysis (relative to anhydrous substance):
Cld: C 59.19 H 7.95 N 9.20
Fnd: C 59.01 H 8.13 N 9.03

EXAMPLE 4

3,6,9-Tris (carboxymethyl)-3,6,9-triazaundecanedioic acid-1-carboxy-11-N-(carboxyundec-11-yl)-amide 35.7 g (100 mmol) of DTPA-bisanhydride is dissolved in 350 ml of dimethyl sulfoxide while 12.72 g (300 mmol) of lithium chloride is added (while heated slightly). It is allowed to cool to 40° C., and a mixture that consists of 20.19 (100 mmol) of 11-aminoundecanoic acid and 40.59 (400 mmol) of triethylamine (dissolved in 50 ml of dimethyl sulfoxide) is added in drops within 30 minutes. It is stirred for 6 hours at 40° C. It is cooled to room temperature, 1.8 g (100 mmol) of water is added, and it is stirred for 10 minutes. A mixture that consists of 200 ml of acetone/2000 ml of methyl-tert-butyl ether (MTB) is added in drops to this solution, and it is stirred for one hour at room temperature. The deposited precipitate is filtered off, washed twice with a little acetone and dried (in a vacuum/50° C.). For purification, it is chromatographed on silica gel (mobile solvent: methanol/chloroform/formic acid 20:10:2). It is absorptively precipitated with isopropanol/formic acid (20:1), the precipitate is suctioned off and dried in a vacuum.

The HPLC of the crude product yielded a monoamide:diamide ratio of 70:30.
Yield: 28.5 g (49% of theory) of a colorless solid
Water content: 0.8%
HPLC purity:>97%
Elementary analysis (relative to anhydrous substance):
Cld: C 52.07 H 7.69 N 9.72
Fnd: C 51.83 H 7.85 N 9.58

EXAMPLE 5

3,6, 9-Tris (carboxymethyl)-3,6,9-triazaundecanedioic acid-1-carboxy-11-N-[(4-methoxy)-phenyl]-amide 35.7 g (100 mmol) of DTPA-bisanhydride is dissolved in 350 ml of dimethyl sulfoxide while 12.72 g (300 mmol) of lithium chloride is added (while heated slightly). It is allowed to cool to 30° C., and a mixture that consists of 12.3 g (100 mmol) of 4-methoxy-aniline and 30.4 g (300 mmol) of triethylamine (dissolved in 20 ml of dimethyl sulfoxide) is added in drops within 30 minutes. It is stirred for 4 hours at 30° C. It is cooled to room temperature, 1.8 g (100 mmol) of water is added, and it is stirred for 10 minutes. A mixture that consists of 100 ml of acetone/2000 ml of methyl-tert-butyl ether (MTB) is added in drops to this solution, and it is stirred for one hour at room temperature. The deposited precipitate is filtered off, washed twice with a little acetone and dried (in a vacuum/50° C.). For purification, it is chromatographed on silica gel (mobile solvent: methanol/chloroform/formic acid=20:15:1). It is absorptively precipitated with isopropanol/formic acid (20:1), the precipitate is suctioned off and dried in a vacuum/60° C.

The HPLC of the crude product yielded a monoamide:diamide ratio of 71:29.

Yield: 26.6 g (53% of theory) of a colorless solid
Water content: 0.7%
HPLC purity:>97%
Elementary analysis (relative to anhydrous substance):
Cld: C 50.60 H 6.07 N 11.24
Fnd: C 50.43 H 6.19 N 11.10

EXAMPLE 6

Bis[3,6,9-tris(carboxymethyl)-3,6,9-triazaundecanedioic acid-1-carboxy-11-amide]-N,N'-[1,4-bis(aminomethyl)-phenyl]-amide 35.7 g (100 mmol) of DTPA-bisanhydride is dissolved in 350 ml of dimethyl sulfoxide while 12.72 g (300 mmol) of lithium chloride is added (while heated slightly). It is allowed to cool to 30° C., and a mixture that consists of 6.8 g (50 mmol) of 1,4-bis(aminomethyl)-benzene and 30.4 g (300 mmol) of triethylamine (dissolved in 20 ml of dimethyl sulfoxide) is added in drops within 30 minutes. It is stirred for 5 hours at 30° C. It is cooled to room temperature, 1.8 g (100 mmol) of water is added, and it is stirred for 10 minutes. A mixture that consists of 200 ml of acetone/2000 ml of methyl-tert-butyl ether (MTB) is added in drops to this solution, and it is stirred for one hour at room temperature. The deposited precipitate is filtered off, washed twice with a little acetone and dried (in a vacuum/50° C.). For purification, it is chromatographed on silica gel (mobile solvent: methanol/chloroform/formic acid=20:5:1). It is absorptively precipitated with isopropanol/formic acid (20:1), the precipitate is suctioned off, and it is dried in a vacuum/60° C.

The HPLC of the crude product yielded a ratio of bis(monoamide):other amides of 49:51.

Yield: 19.2 g (43% of theory relative to the diamine that is used) of a colorless solid
Water content: 0.8%
HPLC purity:>96%
Elementary analysis (relative to anhydrous substance):
Cld: C 48.76 H 6.14 N 12.63
Fnd: C 48.58 H 6.31 N 12.49

EXAMPLE 7

Bis[3,6,9-tris(carboxymethyl)-3,6,9-triazaundecanedioic acid-1-carboxy-11-amide]-N,N'-[1,4-diaminobutane 35.7 g (100 mmol) of DTPA-bisanhydride is dissolved in 350 ml of dimethyl sulfoxide while 26.1 g (300 mmol) of lithium chloride is added (while heated slightly). It is allowed to cool to 35° C., and a mixture that consists of 4.4 g (50 mmol) of 1,4-diaminobutane and 23.7 g (300 mmol) of pyridine (dissolved in 20 ml of dimethyl sulfoxide) is added in drops within 30 minutes. It is stirred for 5 hours at 35° C. It is cooled to room temperature, 1.8 g (100 mmol) of water is added, and it is stirred for 10 minutes. A mixture that consists of 100 ml of acetone/2000 ml of methyl-tert-butyl ether (MTB) is added in drops to this solution, and it is stirred for one hour at room temperature. The deposited precipitate is filtered off, washed twice with a little acetone and dried (in a vacuum/50° C.). For purification, it is chromatographed on silica gel (mobile solvent: methanol/chloroform/formic acid=20:5:1). It is absorptively precipitated with isopropanol/formic acid (20:1), the precipitate is suctioned off and dried in a vacuum/70° C.

The HPLC of the crude product yielded a ratio of monoamide:other amides of 50:50.

Yield: 18.6 g (44% of theory relative to the diamine that is used) of a colorless solid
Water content: 0.9%
HPLC purity:>96%
Elementary analysis (relative to anhydrous substance):
Cld: C 45.82 H 6.49 N 13.36
Fnd: C 45.61 H 6.67 N 13.20

EXAMPLE 8

3,6,9-Tris (carboxymethyl)-3,6,9-triazaundecanedioic acid-1-carboxy-N-[(3-trifluoromethyl)-phenyl]-amide 35.7 g (100 mmol) of DTPA-bisanhydride is dissolved in 350 ml of dimethylformamide while 47.6 g (700 mmol) of imidazole is added (while heated slightly). It is allowed to cool to 50° C., and 14.7 g (100 mmol) of 3-trifluoromethyl-aniline (dissolved in 20 ml of dimethylformamide) is added in drops within 30 minutes. It is stirred for 4 hours at 50° C. It is cooled to room temperature, 1.8 g (100 mmol) of water is added, and it is stirred for 10 minutes. A mixture that consists of 200 ml of acetone/2000 ml of methyl-tert-butyl ether (MTB) is added in drops to this solution, and it is stirred for one hour at room temperature. The deposited precipitate is filtered off, washed twice with a little acetone and dried (in a vacuum/50° C.). For purification, it is chromatographed on silica gel (mobile solvent: methanol/chloroform/formic acid=15:10:1). It is absorptively precipitated with isopropanol/formic acid (20:1), the precipitate is suctioned off, and dried in a vacuum/60° C.

The HPLC of the crude product yielded a monoamide:diamide ratio of 71:29.

Yield: 27.5 g (51% of theory) of a colorless solid
Water content: 0.6%
HPLC purity:>97%
Elementary analysis (relative to anhydrous substance):
Cld: C 47.02 H 5.07 N 10.44
Fnd: C 47.18 H 5.19 N 10.21

EXAMPLE 9

7,12-Diethyl-3,8,13,17-tetramethyl-2,18-bis{3,6,18-trioxo-8,11,14-tris(carboxymethyl)-4,5,8,11,14-pentaazahexadecyl}-porphyrin 17.85 g (50 mmol) of DTPA-bisanhydride is dissolved in 350 ml of dimethyl sulfoxide while 6.36 g (150 mmol) of lithium chloride is added (while heated slightly). It is allowed to cool to 50° C., and a mixture that consists of 14.9 g (25 mmol) and 23.7 g (300 mmol) of mesoporphyrin-IX-13,17-dihydrazide [analogously to H. Fischer, E. Haarer and F. Stadler, Z. Physiol. Chem. 241, 209 (1936)] and 31.6 g (400 mmol) of pyridine is added within 30 minutes. It is stirred for 4 hours at 50° C. It is cooled to room temperature, 3.6 g (200 mmol) of water is added, and it is stirred for 10 minutes. A mixture that consists of 200 ml of acetone/1800 ml of methyl-tert-butyl ether (MTB) is added in drops to this solution, and it is stirred for one hour at room temperature. The deposited precipitate is filtered off, washed twice with a little acetone and dried (in a vacuum/50° C.). For purification, it is chromatographed on silica gel (mobile solvent: methanol/chloroform/formic acid=10:10:1). It is absorptively precipitated with isopropanol/formic acid (20:1), the precipitate is suctioned off, and it is dried in a vacuum/60° C.

The HPLC of the crude product yielded a monoamide:diamide ratio of 68:32.

Yield: 18.1 g (51% of theory, relative to bis-anhydride) of a dark-violet solid
Water content: 0.7%
HPLC purity:>97%
Elementary analysis (relative to anhydrous substance):
Cld: C 55.35 H 6.29 N 14.57
Fnd: C 55.43 H 6.45 N 14.37

EXAMPLE 10
{mu-[{16,16'-[Copper(II)-7,12-diethyl-3,8,13,17-tetramethylporphyrin-2,18-diyl]-bis[3,6,9-tris(carboxymethyl)-11,14-dioxo-3,6,9,12,13-pentazahexadecyl]}-porphyrin 17.85 g (50 mmol) of DTPA-bisanhydride is dissolved in 350 ml of dimethyl sulfoxide while 6.36 g (150 mmol) of lithium chloride is added (while heated slightly). It is allowed to cool to 50° C., and a mixture that consists of 16.49 (25 mmol) of copper-mesoporphyrin-IX-13,17-dihydrazide and 31.6 g (400 mmol) of pyridine is added in drops within 30 minutes. It is stirred for 4 hours at 50° C. It is cooled to room temperature, 3.6 g (200 mmol) of water is added, and it is stirred for 10 minutes. A mixture that consists of 200 ml of acetone/1800 ml of methyl-tert-butyl ether (MTB) is added in drops to this solution, and it is stirred for one hour at room temperature. The deposited precipitate is filtered off, washed twice with a little acetone and dried (in a vacuum/50° C). For purification, it is chromatographed on silica gel (mobile solvent: methanol/chloroform/formic acid 10:10:1). It is absorptively precipitated with isopropanol/formic acid (20:1), the precipitate is suctioned off and dried in a vacuum/60° C.

The HPLC of the crude product yielded a bis(monoamide) :diamide ratio of 69:31.
Yield: 18.4 g (52% of theory relative to bis-hydrazide) of a deep red solid
Water content: 0.8%
HPLC purity:>97%
Elementary analysis (relative to anhydrous substance):
Cld: C 52.93 H 5.87 N 13.94 Cu 4.52
Fnd: C 52.78 H 6.03 N 13.81 Cu 4.38

EXAMPLE 11
3,6,9-Tris(carboxymethyl)-3,6,9-triazaundecanedioic acid-1-carboxy-11-N-[(2-methoxycarbonyl)-phenyl]-amide 35.7 g (100 mmol) of DTPA-bisanhydride is dissolved in 350 ml of dimethyl sulfoxide while 12.72 g (300 mmol) of lithium chloride is added (while heated slightly). It is allowed to cool to 35° C., and a mixture that consists of 15.12 g (100 mmol) of 2-aminobenzoic acid methyl ester and 23.7 g (300 mmol) of pyridine (dissolved in 25 ml of dimethyl sulfoxide) is added in drops within 30 minutes. It is stirred for 5 hours at 35° C. It is cooled to room temperature, 1.8 g (100 mmol) of water is added, and it is stirred for 10 minutes. A mixture that consists of 200 ml of acetone/2000 ml of methyl-tert-butyl ether (MTB) is added in drops to this solution, and it is stirred for one hour at room temperature. The deposited precipitate is filtered off, washed twice with a little acetone, and it is dried (in a vacuum/50° C.). For purification, it is chromatographed on silica gel (mobile solvent: methanol/chloroform/formic acid= 20:20:2). It is stirred with acetone/formic acid (20:1), the precipitate is suctioned off, and it is dried in a vacuum/60° C.

The HPLC of the crude product yielded a ratio of monoamide:diamide of 69:31.
Yield: 27.4 g (52% of theory) of a colorless solid
Water content: 0.6%
HPLC purity:>97%
Elementary analysis (relative to anhydrous substance):
Cld: C 50.19 H 5.74 N 10.64
Fnd: C 50.31 H 5.86 N 10.73

EXAMPLE 12
3,6,9-Tris(carboxymethyl)-3,6,9-triazaundecanedicic acid-1-carboxy-11-N-(1,2,3,4-tetrahydroquinoline-1-yl)-amide 35.7 g (100 mmol) of DTPA-bisanhydride is dissolved in 350 ml of dimethyl sulfoxide while 26.1 g (300 mmol) of lithium bromide is added (while heated slightly). It is allowed to cool to 40° C., and a mixture that consists of 13.32 g (100 mmol) of 1,2,3,4-tetrahydroquinoline and 20.24 g (200 mmol) of triethylamine is added in drops within 30 minutes. It is stirred for 7 hours at 50° C. It is cooled to room temperature, 1.8 g (100 mmol) of water is added, and it is stirred for 10 minutes. A mixture that consists of 200 ml of acetone/2000 ml of ethyl acetate is added in drops to this solution, and it is stirred for one hour at room temperature. The deposited precipitate is filtered off, washed twice with a little acetone, and it is dried (in a vacuum/50° C.). For purification, it is chromatographed on silica gel (mobile solvent: methanol/chloroform/formic acid=20:10:1). It is absorptively precipitated with isopropanol/formic acid (20:1), the precipitate is suctioned off, and it is dried in a vacuum/60° C.

The HPLC of the crude product yielded a monoamide:diamide ratio of 70:30.
Yield: 27.0 g (53% of theory) of a colorless solid
Water content: 0.8% of theory
HPLC purity:>97%
Elementary analysis (relative to anhydrous substance):
Cld: C 54.32 H 6.34 N 11.02
Fnd: C 54.21 H 6.40 N 11.16

EXAMPLE 13
3,6,9-Tris(carboxymethyl)-3,6,9-triazaundecanedioic acid-1-carboxy-11-N-[(2-ethoxy)-ethyl]-amide 35.7 g (100 mmol) of DTPA-bisanhydride is dissolved in 350 ml of dimethylformamide while 54.5 g (800 mmol) of imidazole is added (while heated slightly). It is allowed to cool to 50° C., and a mixture that consists of 8.91 g (100 mmol) of 2-(aminoethyl)-ethyl ether and 23.7 g (300 mmol) of pyridine (dissolved in 20 ml of dimethylformamide) is added in drops within 30 minutes. It is stirred for 4 hours at 50° C. It is cooled to room temperature, 1.8 g (100 mmol) of water is added, and it is stirred for 10 minutes. 2500 ml of acetone is added in drops to this solution, and it is stirred for one hour at room temperature. The deposited precipitate is filtered off, washed twice with a little acetone, and it is dried (in a vacuum/50° C.). For purification, it is chromatographed on silica gel (mobile solvent: methanol/chloroform/formic acid=15:10:1). It is absorptively precipitated with isopropanol/formic acid (20:1), the precipitate is suctioned off, and it is dried in a vacuum/60° C.

The HPLC of the crude product yielded a ratio of monoamide:diamide of 70:30.
Yield: 23.2 g (50% of theory) of a colorless solid
Water content: 0.9%
HPLC purity:>97%
Elementary analysis (relative to anhydrous substance):
Cld: C 46.55 H 6.94 N 12.06
Fnd: C 46.71 H 7.02 N 11.93

EXAMPLE 14
3,6,9-Tris(carboxymethyl)-3,6,9-triazaundecanedioic acid-1-carboxy-11-N-[(2-methyl)-propionic acid benzyl ester-3-yl]amide 35.7 g (100 mmol) of DTPA-bisanhydride is dissolved in 350 ml of dimethyl sulfoxide while 12.72 g (300 mmol) of lithium chloride is added (while heated slightly). It is allowed to cool to 30° C., and a mixture that consists of 15.92 g (100 mmol) of 2-(aminomethyl-propionic acid benzyl ester and 30.4 g (300 mmol) of triethylamine (dissolved in 20 ml of dimethyl sulfoxide) is added in drops within 30 minutes. It is stirred for 4 hours at 30° C. It is cooled to room temperature, 1.8 g (100 mmol) of water is added, and it is stirred for 10 minutes. A mixture that consists of 100 ml of acetone/2000 ml of methyl-tert-butyl ether (MTB) is added in drops to this solution, and it is stirred for one hour at room temperature. The deposited precipitate is filtered off, washed twice with a little acetone, and it is dried (in a vacuum/50° C.) For purification, it is chromatographed on silica gel (mobile solvent: methanol/chloroform/formic acid= 20:15:1). It is absorptively precipitated with isopropanol/formic acid (20:1), the precipitate is suctioned off, and it is dried in a vacuum/60° C.

The HPLC of the crude product yielded a monoamide:diamide ratio of 68:32.

Yield: 29.0 g (51% of theory) of a colorless solid
Water content: 0.7%
HPLC purity:>97%
Elementary analysis (relative to anhydrous substance):
Cld: C 52.81 H 6.38 N 9.85
Fnd: C 52.95 H 6.51 N 10.00

EXAMPLE 15
3,6,9-Tris(carboxymethyl)-3,6,9-triazaundecanedioic acid-1-carboxy-11-N-(benzyl)-amide 35.7 g (100 mmol) of DTPA-bisanhydride is dissolved in 350 ml of dimethylformamide while 54.5 g (800 mmol) of imidazole is added (while heated slightly). It is allowed to cool to 50° C., and a mixture that consists of 10.72 g (100 mmol) of benzylamine and 20.24 g (200 mmol) of triethylamine (dissolved in 20 ml of dimethylformamide) is added in drops within 30 minutes. It is stirred for 4 hours at 50° C. It is cooled to room temperature, 1.8 g (100 mmol) of water is added, and it is stirred for 10 minutes. 2500 ml of acetone is added in drops to this solution, and it is stirred for one hour at room temperature. The deposited precipitate is filtered off, washed twice with a little acetone, and it is dried (in a vacuum/50° C.). For purification, it is chromatographed on silica gel (mobile solvent: methanol/chloroform/formic acid=15:10:1). It is absorptively precipitated with isopropanol/formic acid (20:1), the precipitate is suctioned off, and it is dried in a vacuum/60° C.

The HPLC of the crude product yielded a ratio of monoamide:diamide of 70:30.

Yield: 24.10 g (50% of theory) of a colorless solid
Water content: 0.8%
HPLC purity:>97%
Elementary analysis (relative to anhydrous substance):
Cld: C 50.28 H 6.27 N 11.61
Fnd: C 50.42 H 6.39 N 11.74

EXAMPLE 16
3,6,9-Tris(carboxymethyl)-3,6,9-triazaundecanedioic acid-1-carboxy-11-N-(anthracene-9-yl)-amide 35.7 g (100 mmol) of DTPA-bisanhydride is dissolved in 350 ml of dimethyl sulfoxide while 26.1 g (300 mmol) of lithium bromide is added (while heated slightly). It is allowed to cool to 35° C., and a mixture that consists of 19.33 g (100 mmol) of 9-aminoanthracene and 23.7 g (300 mmol) of pyridine (dissolved in 25 ml of dimethyl sulfoxide) is added in drops within 30 minutes. It is stirred for 6 hours at 50° C. It is cooled to room temperature, 1.8 g (100 mmol) of water is added, and it is stirred for 10 minutes. A mixture that consists of 200 ml of acetone/2000 ml of methyl-tert-butyl ether (MTB) is added in drops to this solution, and it is stirred for one hour at room temperature. The deposited precipitate is filtered off, washed twice with a little acetone, and it is dried (in a vacuum/50° C.). For purification, it is chromatographed on silica gel (mobile solvent: methanol/chloroform/formic acid=20:20:2). It is absorptively precipitated with acetone/formic acid (20:1), the precipitate is suctioned off, and it is dried in a vacuum/60° C.

The HPLC of the crude product yielded a monoamide:diamide ratio of 69:31.

Yield: 29.6 g (49% of theory) of a colorless solid
Water content: 0.9%
HPLC purity:>98%
Elementary analysis (relative to anhydrous substance):
Cld: C 59.15 H 5.67 N 9.85
Fnd: C 59.03 H 5.77 N 9.98

EXAMPLE 17
3,6,9-Tris(carboxymethyl)-3,6,9-triazaundecanedioic acid-1-carboxy-11-N-(tbutyloxy-carbonylmethyl)-amide 35.7 G (100 mmol) of DTPA-bisanhydride is dissolved in 350 ml of dimethyl sulfoxide while 84.4 g (600 mmol) of 4-nitrophenol is added (while heated slightly). It is allowed to cool to 30° C., and a mixture that consists of 13.12 g (100 mmol) of glycine-tbutyl ester and 71.2 g (900 mmol) of pyridine (dissolved in 20 ml of dimethyl sulfoxide) is added in drops within 30 minutes. It is stirred for 4 hours at 50° C. It is cooled to room temperature, 1.8 g (100 mmol) of water is added, and it is stirred for 10 minutes. A mixture that consists of 100 ml of acetone/2000 ml of methyl-tert-butyl ether (MTB) is added in drops to this solution, and it is stirred for one hour at room temperature. The deposited precipitate is filtered off, washed twice with a little acetone, and it is dried (in a vacuum/50° C.). For purification, it is chromatographed on silica gel (mobile solvent: methanol/chloroform/formic acid=20:15:1). It is absorptively precipitated with isopropanol/formic acid (20:1), the precipitate is suctioned off, and it is dried in a vacuum/60° C.

The HPLC of the crude product yielded a monoamide:diamide ratio of 68:32.

Yield: 26.8 g (53% of theory) of a colorless solid
Water content: 0.7%
HPLC purity:>97%
Elementary analysis (relative to anhydrous substance):
Cld: C 47.43 H 6.77 N 11.06
Fnd: C 47.57 H 6.89 N 11.15

EXAMPLE 18
3,6,9-Tris(carboxymethyl)-3,6,9-triazaundecanedioic acid-1-carboxy-N-[(4-trifluoromethyl)-phenyl]-amide 35.7 g (100 mmol) of DTPA-bisanhydride is dissolved in 350 ml of dimethyl sulfoxide while 12.72 g (300 mmol) of lithium chloride is added (while heated slightly). It is allowed to cool to 30° C., and a mixture that consists of 14.7 g (100 mmol) of 4-trifluoromethylaniline and 55.6 g (300 mmol) of tributylamine (dissolved in 20 ml of dimethyl sulfoxide) is added in drops within 30 minutes. It is stirred for 5 hours at 40° C. It is cooled to room temperature, 1.8 g (100 mmol) of water is added, and it is stirred for 10 minutes. A mixture that consists of 100 ml of acetone/100 ml of ethyl acetate is added in drops to this solution, and it is stirred for one hour at room temperature. The deposited precipitate is filtered off, washed twice with a little acetone, and it is dried (in a vacuum/50° C). For purification, it is chromatographed on silica gel (mobile solvent: methanol/chloroform/formic acid=20:15:1) It is absorptively precipitated with isopropanol/formic acid (20:1), the precipitate is suctioned off, and it is dried in a vacuum/60° C.

The HPLC of the crude product yielded a ratio of monoamide:diamide of 72:28.

Yield: 26.3 g (49% of theory) of a colorless solid
Water content: 0.6%
HPLC purity:>97%
The HPLC of the crude product yielded a ratio of monoamide:diamide of 72:28.
Yield: 26.3 g (49% of theory) of a colorless solid
Water content: 0.6%
HPLC purity:>97%
Elementary analysis (relative to anhydrous substance):
Cld: C 47.02 H 5.07 N 10.44
Fnd: C 47.16 H 5.18 N 10.23

EXAMPLE 19
3,6,9-Tris(carboxymethyl)-3,6,9-triazaundecanedioic acid-1-carboxy-11-N-[(4-ethoxy-carbonyl)-cyclohexyl]-amide 35.7 g (100 mmol) of DTPA-bisanhydride is dissolved in 350 ml of dimethyl sulfoxide while 26.1 g (300 mmol) of lithium bromide is added (while heated slightly). It is allowed to cool to 30° C., and a mixture that consists of 17.12 g (100 mmol) of 4-amino-cyclohexanecarboxylic acid ethyl ester and 30.4 g (300 mmol) of triethylamine (dissolved in 20 ml of dimethyl sulfoxide) is added in drops within 30 minutes. It is stirred for 6 hours at 50° C. It is cooled to room temperature, 1.8 g (100 mmol) of water is added, and it is stirred for 10 minutes. A mixture that consists of 100 ml of acetone/2000 ml of methyl-tert-butyl ether (MTB) is added in drops to this solution, and it is stirred for one hour at room temperature. The deposited precipitate is filtered off, washed twice with a little acetone, and it is dried (in a vacuum/50° C.) For purification, it is chromatographed on silica gel (mobile solvent: methanol/chloroform/formic acid=20:15:1). It is absorptively precipitated with isopropanol/formic acid (20:1), the precipitate is suctioned off, and it is dried in a vacuum/60° C. The HPLC of the crude product yielded a ratio of monoamide:diamide of 67:33.

Yield: 27.3 g (50% of theory) of a colorless solid
Water content: 0.6%
HPLC purity:>98%
Elementary analysis (relative to anhydrous substance):
Cld: C 50.54 H 7.01 N 10.25
Fnd: C 50.67 H 7.12 N 10.17

EXAMPLE 20
3,6,9-Tris(carboxymethyl)-3,6,9-triazaundecanedioic acid-1-carboxy-11-N,N-dibutyl-amide 35.7 g (100 mmol) of DTPA-bisanhydride is dissolved in 350 ml of dimethyl sulfoxide while 26.10 g (300 mmol) of lithium bromide is added (while heated slightly). It is allowed to cool to 40° C., and a mixture that consists of 12.93 g (100 mmol) of dibutylamine and 20.24 g (200 mmol) of triethylamine is added in drops within 30 minutes. It is stirred for 8 hours at 40° C. It is cooled to room temperature, 1.8 g (100 mmol) of water is added, and it is stirred for 10 minutes. A mixture that consists of 200 ml of acetone/1800 ml of methyl-tert-butyl ether (MTB) is added in drops to this solution, and it is stirred for one hour at room temperature. The deposited precipitate is filtered off, washed twice with a little acetone, and it is dried (in a vacuum/50° C.). For purification, it is chromatographed on silica gel (mobile solvent: methanol/chloroform/formic acid=20:10:1). It is absorptively precipitated with isopropanol/formic acid (20:1), the precipitate is suctioned off, and it is dried in a vacuum/60° C. The HPLC of, the crude product yielded a monoamide:diamide ratio of 69:31.

Yield: 25.7 g (51% of theory) of a colorless solid
Water content: 0.8% of theory
HPLC purity:>97%
Elementary analysis (relative to anhydrous substance):
Cld: C 52.37 H 7.99 N 11.10
Fnd: C 52.46 H 8.13 N 11.00

EXAMPLE 21
3,6,9-Tris(carboxymethyl)-3,6,9-triazaundecanedioic acid-1-carboxy-11-N-[(4-phenyl)-piperidine]-amide 35.7 g (100 mmol) of DTPA-bisanhydride is dissolved in 350 ml of dimethyl sulfoxide while 54.5 g (800 mmol) of lithium chloride is added (while heated slightly). It is allowed to cool to 30° C., and a mixture that consists of 16.13 g (100 mmol) of 4-phenylpiperidine and 27.3 g (300 mmol) of pyridine (dissolved in 20 ml of dimethyl sulfoxide) is added in drops within 30 minutes. It is stirred for 6 hours at 50° C. It is cooled to room temperature, 1.8 g (100 mmol) of water is added, and it is stirred for 10 minutes. A mixture that consists of 100 ml of acetone/2000 ml of methyl-tert-butyl ether (MTB) is added in drops to this solution, and it is stirred for one hour at room temperature. The deposited precipitate is filtered off, washed twice with a little acetone, and it is dried (in a vacuum/50° C.) For purification, it is chromatographed on silica gel (mobile solvent: methanol/chloroform/formic acid=20:15:1). It is absorptively precipitated with isopropanol/formic acid (20:1), the precipitate is suctioned off, and it is dried in a vacuum/60° C.

The HPLC of the crude product yielded a monoamide:diamide ratio of 72:28.

Yield: 27.9 (52% of theory) of a colorless solid
Water content: 0.7%
HPLC purity:>97%
Elementary analysis (relative to anhydrous substance):
Cld: C 55.96 H 6.76 N 10.44
Fnd: C 56.11 H 6.90 N 10.57

EXAMPLE 22
3,6,9-Tris(carboxymethyl)-3,6,9-triazaundecanedioic acid-1-carboxy-11-N-methyl-N-[methyl-(2,2-dimethyl-1,3-dioxolane-4-yl)]-amide 35.7 g (100 mmol) of DTPA-bisanhydride is dissolved in 350 ml of dimethyl sulfoxide while 26.1 g (300 mmol) of lithium bromide is added (while heated slightly). It is allowed to cool to 40° C., and a mixture that consists of 14.42 g (100 mmol) of 4-(methylamino)-methyl-2,2-dimethyl-1,3-dioxolane and 20.24 (200 mmol) of triethylamine is added in drops within 30 minutes. It is stirred for 6 hours at 40° C. It is cooled to room temperature, 1.8 g (100 mmol) of water is added, and it is stirred for 10 minutes. 2500 ml of acetone is added in drops to this solution, and it is stirred for one hour at room temperature. The deposited precipitate is filtered off, it is washed twice with a little acetone, and it is dried (in a vacuum/50° C.). For purification, it is chromatographed on silica gel (mobile solvent: methanol/chloroform/formic acid=20:10:1). It is absorptively precipitated with isopropanol/formic acid (20:1), the precipitate is suctioned off, and it is dried in a vacuum/60° C.

The HPLC of the crude product yielded a monoamide:diamide ratio of 68:32.

Yield: 27.1 g (52% of theory) of a colorless solid
Water content: 0.8% of theory
HPLC purity:>97%
Elementary analysis (relative to anhydrous substance):
Cld: C 48.46 H 6.97 N 10.76
Fnd: C 48.58 H 7.11 N 10.92

EXAMPLE 23

3,6,9-Tris(carboxymethyl)-3,6,9-triazaundecanedioic acid-1-carboxy-11-N-[2-(tbutyloxy-carbonylmethyl)-2-(4-hydroxy)-phenyl]-amide 35.7 g (100 mmol) of DTPA-bisanhydride is dissolved in 350 ml of dimethyl sulfoxide while 26.1 g (300 mmol) of lithium bromide is added (while heated slightly). It is allowed to cool to 35° C., and a mixture that consists of 23.73 g (100 mmol) of 3-(4-hydroxyphenyl)-2-aminopropionic acid-tbutyl ester and 23.7 g (300 mmol) of pyridine (dissolved in 25 ml of dimethyl sulfoxide) is added in drops within 30 minutes. It is stirred for 5 hours at 40° C. It is cooled to room temperature, 1.8 g (100 mmol) of water is added, and it is stirred for 10 minutes. A mixture that consists of 200 ml of acetone/2000 ml of methyl-tert-butyl ether (MTB) is added in drops to this solution, and it is stirred for one hour at room temperature. The deposited precipitate is filtered off, it is washed twice with a little acetone, and it is dried (in a vacuum/50° C.). For purification, it is chromatographed on silica gel (mobile solvent: methanol/chloroform/formic acid=20:20:2). It is absorptively precipitated with acetone/formic acid (20:1), the precipitate is suctioned off, and it is dried in a vacuum/60° C.

The HPLC of the crude product yielded a monoamide:diamide ratio of 70:30.

Yield: 31.1 g (52% of theory) of a colorless solid
Water content: 0.9%
HPLC purity:>98%
Elementary analysis (relative to anhydrous substance):
Cld: C 52.17 H 6.40 N 9.36
Fnd: C 52.02 H 6.51 N 9.50

In the following table, various methods of monoamide formation from DTPA-bisanhydride and amine are compared with respect to their selectivity of monoamide formation.

Selectivity of Amide Formation

| A(H)$_n$ | Monamide/Bisamide Ratio | | | | Reaction Conditions D Solvent Solubilizer Temperature/Time Auxiliary base Precipitating agent |
|---|---|---|---|---|---|
| | A | B | C | D | |
| aniline (C$_6$H$_5$NH$_2$) | 11:89 | 5:95 | 31:69 | 70:30 | DMSO<br>LiCl(3 eq.)<br>20° C./5 hours<br>pyridine<br>acetone (10 × DMSO volume) |
| morpholine | 10:90 | 8:92 | 37:63 | 71:29 | DMF<br>imidazole (8 eq.)<br>50° C./50 hours<br>pyridine<br>MTB (10 × DMSO volume) |
| methyl 2-aminobenzoate | 5:95 | 5:95 | 35:65 | 69:31 | DMSO<br>LiCl (3 eq.)<br>30° C./6 hours<br>pyridine<br>MTB (10 × DMSO volume) |
| 1,2,3,4-tetrahydroquinoline | 5:95 | 3:97 | 38:62 | 70:30 | DMSO<br>LiBr/7 hours<br>50° C.<br>NEt$_3$, ethyl acetate<br>(10 × DMSO volume) |
| 2-ethoxyethylamine | 15:85 | 10:90 | 20:80 | 70:30 | DMF<br>imidazole (8 eq.)<br>50° C./5 hours<br>pyridine<br>acetone (10 × DMF volume) |

-continued

| A(H)$_n$ | Monamide/Bisamide Ratio | | | | Reaction Conditions D Solvent Solubilizer Temperature/ Time Auxiliary base Precipitating agent |
|---|---|---|---|---|---|
| | A | B | C | D | |
| 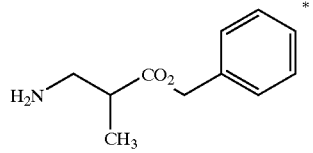 | 5:95 | 3:97 | 38:62 | 68:32 | DSMO<br>LiCl (3 eq.)<br>40° C./4 hours<br>NEt$_3$ acetone<br>(8 × DMSO volume) |
| 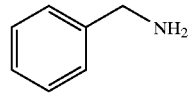 | 10:90 | 5:95 | 39:61 | 70:30 | DMF<br>Imidazole (8 eq.)<br>45° C./6 hours<br>NEt$_3$ acetone<br>(10 × DMF volume) |
| 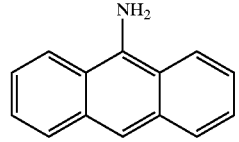 | 5:95 | 5:95 | 31:69 | 69:31 | DMSO<br>LiBr<br>50° C./6 hours<br>pyridine<br>MTB (12 ×<br>DMSO volume) |
| 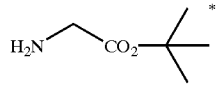 | 12:88 | 10:90 | 35:65 | 68:32 | DMSO<br>4-nitrophenol<br>(6 eq.)<br>50° C./4 hours<br>pyridine,<br>MTB (12 ×<br>DMSO volume) |
| 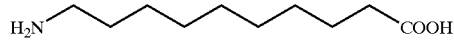 | 17:83 | 10:90 | 29:71 | 70:30 | DMSO<br>LiCl (3 eq.)<br>50° C./5 hours<br>pyridine,<br>MTB (12 ×<br>DMSO volume) |
| 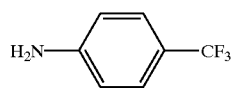 | 15:85 | 5:95 | 34:66 | 72:28 | DMSO<br>LiCl (3 eq.)<br>40° C./5 hours<br>N(Bu)$_3$ ethyl<br>acetate<br>(8 × DMSO volume) |
| 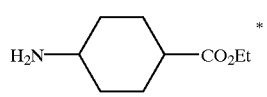 | 10:90 | 5:95 | 35:65 | 67:33 | DMSO<br>LiBr (3 eq.)<br>50° C./6 hours<br>NEt$_3$ MTB<br>(10 ×<br>DMSO volume) |
| 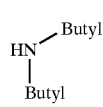 | 10:90 | 5:95 | 30:70 | 69:31 | DMSO<br>LiCl (3 eq.)<br>40° C./8 hours<br>NEt$_3$ acetone<br>(10 × DMSO volume) |
| 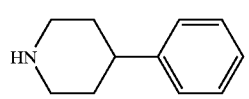 | 15:85 | 3:97 | 25:75 | 72:28 | DMF<br>Imidazole (8 eq.)<br>50° C./6 hours<br>pyridine<br>MTB (10 ×<br>DMSO volume) |

-continued

| A(H)$_n$ | Monamide/Bisamide Ratio | | | | Reaction Conditions D Solvent Solubilizer Temperature/Time Auxiliary base Precipitating agent |
|---|---|---|---|---|---|
| | A | B | C | D | |
| [structure: CH$_3$-NH-CH$_2$-CH(O-)-CH$_2$-O- cyclic with CH$_3$ acetal] | 13:87 | 10:90 | 17:83 | 68:32 | DMSO<br>LiCl<br>50° C. (3 eq.)<br>NEt$_3$ acetone<br>(15 × DMSO volume) |
| [structure: HO-C$_6$H$_4$-CH$_2$-CH(NH$_2$)-CO$_2$-tBu] | 5:95 | 10:90 | 35:65 | 70:30 | DMSO<br>LiBr<br>40° C./5 hours<br>pyridine<br>MTB (15 × DMSO volume) |
| [structure: 3-CF$_3$-C$_6$H$_4$-NH$_2$] | 14:86 | 5:95 | 34:66 | 71:29 | DMF<br>imidazole (8 eq.)<br>50° C./4 hours<br>pyridine<br>MTB (10 × DMF volume) |
| [structure: CH$_3$O-C$_6$H$_4$-NH$_2$] | 10:90 | 6:94 | 38:62 | 71:29 | DMSO<br>LiCl (3 eq.)<br>30°/4 hours<br>NEt$_3$ MTB<br>(10 × DMSO volume) |
| [structure: C$_{10}$H$_{21}$-C$_6$H$_4$-NH$_2$] | 16:84 | 8:92 | 32:68 | 70:30 | DMSO<br>LiCl (3 eq.)<br>35° C./5 hours<br>pyridine<br>MTB (10 × DMSO volume) |

*The given ratio for A, B and C relates to the sum of wanted product and hydrolysis product.

Mobile solvent: column: Hy purity elite Sum 5 μm, 150×3.0 mm
Gradient 5% acetonitrile in H$_2$O—95% acetonitrile in H$_2$O
Flow rate: 0.4 ml/min
Detector: VV 242 nm
Temperature: room temperature

| Process A: | Reaction of amine/large excess of anhydride in DMF, (U.S. Pat. No. 5274082) |
|---|---|
| Process B: | Reaction of amine/small excess of anhydride,: without solubilizer in DMSO, (WO 96/00079) |
| Process C: | Reaction of amine/anhydride 1:1, without solubilizer in DMSO/Pyr, heating (50° C.), (WO 95/33494) |
| Process D: | Reaction of amine/anhydride 1:1, according to the invention |

General Production Instructions (D)

10.72 g (30 mmol) of DTPA-bisanhydride is dissolved in DMSO (or DMF in cases where imidazole is used as a mediator) while x eq. of solubilizer is added and while heated. It is allowed to cool to the desired temperature (20–50° C.), and the amine A(H)$_n$ (30 mmol) is added in drops together with 60 mmol of an auxiliary base (both optionally dissolved in very little DMSO (DMF)). It is stirred for 3–8 hours at the desired temperature (20°–50° C.). It is cooled to room temperature, 60 mmol of water is added and then precipitated with an organic solvent (depending on the polarity of the amine 5–30×the volume relative to DMSO (DMF)). The precipitates are filtered off and dried in a vacuum (optionally with heating). The crude product that is obtained is characterized by HPLC analysis.

The entire disclosure[s] of all applications, patents and publications, cited herein and of corresponding German application No. 10105014.3-41 filed Jan. 26, 2001, and U.S. Provisional Application Serial No. 60/268,059, filed Feb. 13, 2001, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the preparation of a monoamide of diethylenetriaminepentaacetic acid of formula (I)

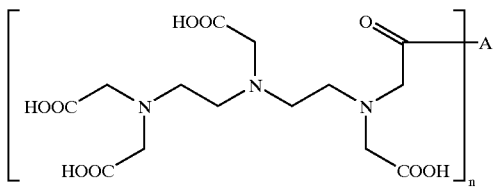

in which
n is 1 or 2,
A is, when n is 1, a primary, secondary, aliphatic, aromatic or araliphatic monoamine attached through N, or
when n is 2, a primary, secondary, mixed primary/secondary, aliphatic, aromatic, araliphatic or mixed aliphatic/aromatic/araliphatic diamine attached through 2 N atoms,
comprising dissolving diethylenetriaminepentaacetic-bisanhydride of formula (2)

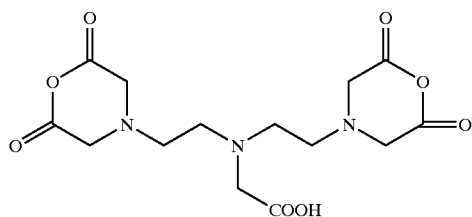

in dimethyl sulfoxide or in dimethylformamide or in a mixture thereof, adding thereto an inorganic or organic solubilizer, an auxiliary base and a monoamine or diamine of formula II, or salt thereof, thereby forming a reaction mixture, $$A(H)_n \quad (II)$$

in which n and A are defined as above, and reacting said reaction mixture at a reaction temperature of 10–70° C. for a reaction time of 1–24 hours, wherein water is not added to the reaction mixture.

2. A process according to claim 1, wherein the monoamine is Aniline, 4-Bromoaniline, 4-Methylaniline, 3-Trifluoromethylaniline, 2-Ethoxycarbonylaniline, 4-Cyclohexylaniline, 4-Decylaniline, 4-Methoxyaniline, 4-Nitroaniline, 4-Phenylaniline, 3,5-Bistrifluoromethylaniline, $CH_3$—$(CH_2)_{n=0-9}$—$NH_2$, 5-Aminoisophthalic acid diethyl ester, NH2CH2—CHOH—CHOH—CH2OH, Ammonia, Morpholine, 4-N-(Methylamino-methyl-2,2-dimethyl-1,3-dioxolane, N-(2-Aminoethyl)-morpholine, 4-(4-Fluoro)-phenyl-piperazine, Piperidine, 2-Piperidinocarboxylic acid benzyl ester, 4-Ethoxycarbonylpiperidine, 2-Ethoxyethylamine, 11-Aminoundecanoic acid ethyl ester, 2-Amino-1,3-propanediol, 4-Phenylpiperidine, Indoline, Tetrahydroquinoline, 2-Deoxy-2-aminoglucose, Alanine benzyl ester, Dibutylamine, Glycine-t-butylester, 4-Aminopyridine, Benzylamine, 2-Aminopropionic acid ethyl ester, Cytidine, Adenosine, 2-Phenylethylamine, 9-Aminoacridine, 9-Aminoanthracene, Iminostilbene, Carbazole, 1-Aminoadamantane, 3-Aminomethyl-2,2,5,5-tetramethylpyrrolidine-1-yloxy, or a mixture thereof.

3. A process according to claim 1, wherein the diamine is Hydrazine, $H_2N$—$(CH_2)_{2-2-10}$—$NH_2$, 1,4-Bisaminomethylbenzene, Homopiperazine, 3,6-Diaminoacridine, 4,4'-aminomethylbenzidine, 2,5-Diazabicylo[2.2.1]-heptane, 1,4-diaminocyclohexane, Mesoporphyrin IX-13,17-dihydrazide, Cu-Mesoporphyrin IX-13,17-dihydrazide, or a mixture thereof.

4. A process according to claim 1, wherein 1 to 10 equivalents of the solubilizer are added relative to the diethylenetriaminepentaacetic-bisanhydride of formula (2).

5. A process for the preparation of a monoamide of diethylenetriaminepentaacetic acid of formula (I)

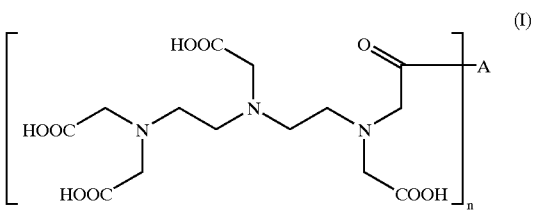

in which
n is 1 or 2,
A is, when n is 1, a primary, secondary, aliphatic, aromatic or araliphatic monoamine attached through N, or
when n is 2, a primary, secondary, mixed primary/secondary, aliphatic, aromatic, araliphatic or mixed aliphatic/aromatic/araliphatic diamine attached through 2 N atoms, comprising dissolving diethylenetriaminepentaacetic-bisanhydride of formula (2)

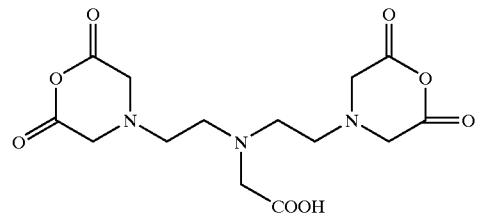

in dimethyl sulfoxide, adding thereto a solubilizer selected from the group consisting of lithium chloride, lithium bromide, lithium iodide, lithium mesylate, lithium tosylate, imidazole, phenylimidazole, N-methyl-imidazole, 4-nitrophenol, pentafluorophenol, N-hydroxysuccinimide, N-hydroxy-phenyl-triazole, or a phase transfer salt of $NR^{4+}$ $Hal^-$, wherein R is a $C_1$–$C_6$ alkyl and Hal is chlorine, iodine or bromine, an auxiliary base and a monoamine or diamine of formula II, or salt thereof, thereby forming a reaction mixture, $$A(H)_n \quad (II)$$

in which n and A are defined as above, and reacting said reaction mixture at a reaction temperature of 10–70° C. for a reaction time of 1–24 hours.

6. A process for the preparation of a monoamide of diethylenetriaminepentaacetic acid of formula (I)

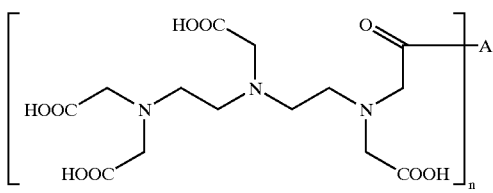

(I)

in which n is 1 or 2,

A is, when n is 1, a primary, secondary, aliphatic, aromatic or araliphatic monoamine attached through N, or when n is 2, a primary, secondary, mixed primary/secondary, aliphatic, aromatic, araliphatic or mixed aliphatic/aromatic/araliphatic diamine attached through 2 N atoms, comprising dissolving diethylenetriaminepentaacetic-bisanhydride of formula (2)

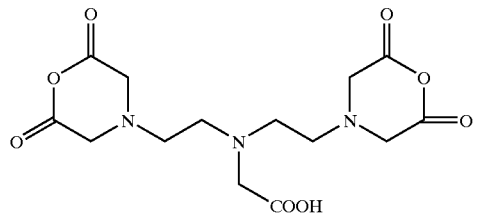

in dimethylformamide, adding thereto imidazole, an auxiliary base and a monoamine or diamine of formula II, or salt thereof, thereby forming a reaction mixture, $A(H)_n$ (II)

in which n and A are defined as above, and reacting said reaction mixture at a reaction temperature of 10–70° C. for a reaction time of 1–24 hours.

7. A process according to claim 1, wherein the auxiliary base is pyridine, triethylamine, N-ethylmorpholine or imidazole.

8. A process according to claim 1, wherein the monoamine is 4-decylaniline or 11-aminoundecanoic acid ethyl ester.

9. A process according to claim 1, wherein the diamine is Mesoporphyrin IX-13,17-dihydrazide or Cu-Mesoporphyrin IX-13,17-dihydrazide.

10. A process according to claim 1, wherein 2 to 5 equivalents of the solubilizer are added relative to the diethylenetriaminepentaacetic-bisanhydride of formula (2).

11. A process according to claim 1, wherein the reaction temperature is 15–50° C.

12. A process according to claim 1, wherein the reaction time is 3–8 hours.

13. A process according to claim 1, wherein the auxiliary base and the monoamine or diamine of formula II is added together.

14. A process according to claim 1, wherein the reaction mixture comprises 30% by weight of diethylenetriaminepentaacetic-bisanhydride.

15. A process according to claim 1, wherein the reaction mixture comprises 20–30% by weight of the solubilizer.

16. A process according to claim 1, further comprising, after the reaction, a step of adding water to the resultant mixture whereby a precipitate is formed, filtering off the precipitate, and purifying said precipitate.

17. A process for the preparation of a monoamide of diethylenetriaminepentaacetic acid of formula (I)

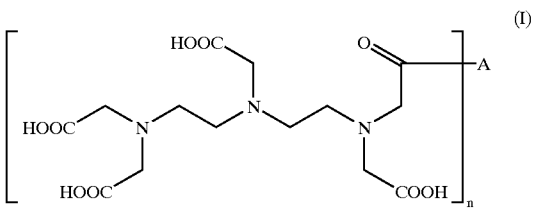

in which n is 2,

A is, a primary, secondary, mixed primary/secondary, aliphatic, aromatic, araliphatic or mixed aliphatic/aromatic/araliphatic diamine attached through 2 N atoms, comprising dissolving diethylenetriaminepentaacetic-bisanhydride of formula (2)

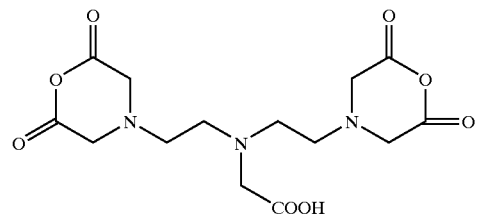

in dimethyl sulfoxide or in dimethylformamide or in a mixture thereof, adding thereto an inorganic or organic solubilizer, an auxiliary base and a monoamine or diamine of formula II, or salt thereof, thereby forming a reaction mixture, $A(H)_n$ (II)

in which n and A are defined as above, and reacting said reaction mixture at a reaction temperature of 10–70° C. for a reaction time of 1–24 hours.

18. A process according to claim 5, wherein the reaction temperature is 15–50° C.

19. A process according to claim 6, wherein the reaction temperature is 15–50° C.

20. A process according to claim 17, wherein the reaction temperature is 15–50° C.

* * * * *

UNITED STATES PATENT AND TRADEMARK OFFICE
CERTIFICATE OF CORRECTION

PATENT NO. : 6,677,483 B2
DATED : January 13, 2004
INVENTOR(S) : Johaness Platzek et al.

It is certified that error appears in the above-identified patent and that said Letters Patent is hereby corrected as shown below:

Column 24,
Line 2, reads "$H_2N\text{--}(CH_2)_{2\text{-}2\text{-}10}$" should read -- $H_2N\text{--}(CH_2)_{N=2\text{-}10}$ --

Signed and Sealed this

Fourteenth Day of September, 2004

JON W. DUDAS
*Director of the United States Patent and Trademark Office*